United States Patent
Thompson et al.

(10) Patent No.: US 8,921,595 B2
(45) Date of Patent: Dec. 30, 2014

(54) PROTEIN ARGININE DEIMINASE INHIBITORS AS NOVEL THERAPEUTICS FOR RHEUMATOID ARTHRITIS AND CANCER

(75) Inventors: Paul R. Thompson, Jupiter, FL (US); Corey P. Causey, Jacksonville, FL (US)

(73) Assignee: University of South Carolina, Columbia, SC (US)

( * ) Notice: Subject to any disclaimer, the term of this patent is extended or adjusted under 35 U.S.C. 154(b) by 295 days.

(21) Appl. No.: 13/503,446

(22) PCT Filed: Oct. 25, 2010

(86) PCT No.: PCT/US2010/053944
§ 371 (c)(1),
(2), (4) Date: Jul. 9, 2012

(87) PCT Pub. No.: WO2011/050357
PCT Pub. Date: Apr. 28, 2011

(65) Prior Publication Data
US 2012/0277176 A1    Nov. 1, 2012

Related U.S. Application Data

(60) Provisional application No. 61/279,657, filed on Oct. 23, 2009.

(51) Int. Cl.
| | | |
|---|---|---|
| A61K 31/205 | (2006.01) | |
| C07C 257/14 | (2006.01) | |
| A61P 35/00 | (2006.01) | |
| C12N 9/99 | (2006.01) | |
| A61K 38/06 | (2006.01) | |
| A61K 31/166 | (2006.01) | |

(52) U.S. Cl.
CPC ............... *A61K 38/06* (2013.01); *A61K 31/166* (2013.01)
USPC .......................................... 562/440; 514/556

(58) Field of Classification Search
None
See application file for complete search history.

(56) References Cited

U.S. PATENT DOCUMENTS

| | | |
|---|---|---|
| 2005/0159334 A1 | 7/2005 | Gluck et al. |
| 2009/0162877 A1 | 6/2009 | Thompson et al. |

FOREIGN PATENT DOCUMENTS

| | | |
|---|---|---|
| WO | WO 2007-056389 | 5/2007 |

OTHER PUBLICATIONS

The Pennsylvania State University, Inhibition of PAD4 with a-amidine or SiRNAs to Inhibit Cancer Cell Growth Through the p53 Pathway, Feb. 5, 2009.*
International Search Report from PCT/US10/053944—3 pages.

* cited by examiner

*Primary Examiner* — Layla Bland
(74) *Attorney, Agent, or Firm* — Dority & Manning, P.A.

(57) ABSTRACT

In accordance with certain embodiments of the present disclosure, a self-assembling biodegradable nanoparticle is provided. The nanoparticle includes Cys-Val-Val-Val-Val-Val-Lys-Lys conjugated with a synthetic polymer and has a diameter of from about 50 nm to about 150 nm.

9 Claims, 7 Drawing Sheets

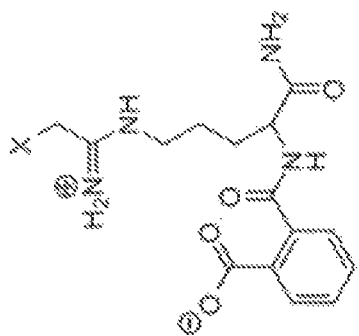
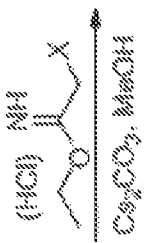
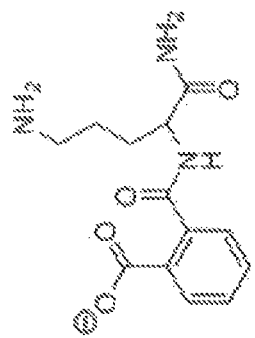
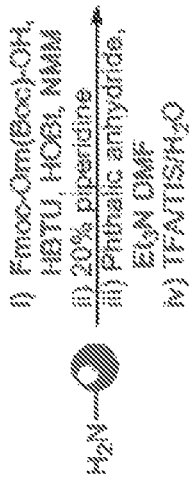
FIG. 3

Table 2. Cytotoxicity of o-F- and o-Cl-amidine in combination with Doxorubicin in HL-60 cells.

| Combination[a] | EC$_{50}$[b] (μM) | % Survival[c] |
|---|---|---|
| Dox | 2.5 ± 1.2 | 12 ± 4.4 |
| Dox + oCA(0.1 μM) | 0.39 ± 0.02 | ND[d] |
| Dox + oCA(1 μM) | 0.34 ± 0.03 | ND[d] |
| Dox + oCA(10 μM) | 0.34 ± 0.12 | ND[d] |
| Dox + oCA(100 μM) | 0.45 ± 0.12 | ND[d] |
| Dox + oFA(1 μM) | 0.44 ± 0.03 | ND[d] |
| Dox + oFA(10 μM) | 0.42 ± 0.007 | ND[d] |
| Dox + oFA (100 μM) | 0.45 ± 0.00008 | ND[d] |

[a] Abbreviations: Doxorubicin (Dox); o-Cl-amidine (oCA); o-F-amidine (oFA). [b] EC$_{50}$ is defined as the concentration of agent that reduces cell viability to 50% of maximum. These values were determined by fitting the dose response data to equation 1. [c] % Survival is based on the cell viability at the maximum agent concentration tested. [d] ND: no viable cells were detected as defined by the lack of absorbance above the 100% killing control.

FIG. 10

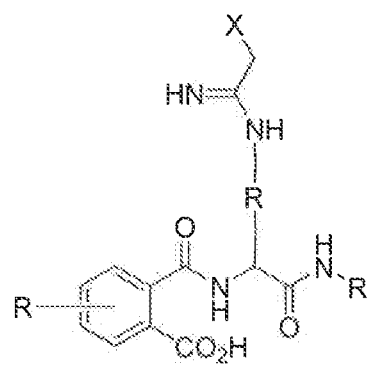

FIG. 8

Table 1. Inhibition of PAD isozymes by haloacetamidine-based inhibitors.

| Compound | Isozyme | IC$_{50}$ (μM) | $k_{inact}$ (min$^{-1}$) | K$_I$ (μM) | $k_{inact}$/K$_I$ (M$^{-1}$min$^{-1}$) |
|---|---|---|---|---|---|
| F-amidine | PAD1 | 29 ± 1.32 | | | |
| | PAD3 | 367 ± 189 | | | |
| | PAD4 | 22 ± 2.10 | 1.0 ± 0.1 | 330 ± 90 | 3000 |
| Cl-amidine | PAD1 | 0.8 ± 0.3 | | | |
| | PAD3 | 6 ± 1.0 | | | |
| | PAD4 | 5.9 ± 0.3 | 2.4 ± 0.2 | 180 ± 33 | 13000 |
| o-F-amidine | PAD1 | 1.4 ± 0.41 | | | |
| | PAD3 | 34 ± 31.9 | | | |
| | PAD4 | 1.9 ± 0.21 | 0.5 ± 0.17 | 16 ± 9 | 32500 |
| o-Cl-amidine | PAD1 | 0.84 ± 0.12 | | | |
| | PAD3 | 0.69 ± 0.34 | | | |
| | PAD4 | 2.2 ± 0.31 | 0.5 ± 0.11 | 13 ± 5.2 | 38000 |

FIG. 9

PROTEIN ARGININE DEIMINASE INHIBITORS AS NOVEL THERAPEUTICS FOR RHEUMATOID ARTHRITIS AND CANCER

CROSS-REFERENCE TO RELATED APPLICATION

The present application is based on and claims priority to International Patent Application PCT/US10/53944 having a filing date of Oct. 25, 2010 based on U.S. Provisional Application 61/279,657 having a filing date of Oct. 23, 2009, which is incorporated by reference herein.

GOVERNMENT SUPPORT CLAUSE

This invention was made with government support under NIH R01GM079357 awarded by National Institutes of Health. The government has certain rights in the invention.

BACKGROUND

Protein Arginine Deiminases (PADs) are calcium dependant enzymes that catalyze the hydrolytic conversion of arginine residues to citrulline residues in a variety of protein substrates as illustrated in FIG. 1. While the five known members of this family, PADs 1, 2, 3, 4, and 6, share a high level (~50%) of sequence homology, their tissue distribution varies widely. Additionally, while, PADs 1-3 and PAD6 are primarily cytoplasmic enzymes, PAD4 is found in both cytoplasmic granules and within cell nuclei. Over the past several years, evidence has emerged suggesting that the dysregulated activity of these enzymes, most notably PAD4, plays a causative role in a number of human diseases, including rheumatoid arthritis (RA), multiple sclerosis (MS), and cancer.

Evidence linking dysregulated PAD activity to rheumatoid arthritis (RA) includes the suggestion that the PAD4 gene represents a susceptibility locus for rheumatoid arthritis (RA) in the Japanese population. While a conclusive link between PAD4 and RA in French, German, and English populations has yet to be demonstrated, the preponderance of evidence from serological and biochemical studies suggests that PAD activity, in general, plays a role in the onset and progression of RA. These data include the fact that the RA-associated HLA-DRB1*0401 MHC class II molecule binds with high affinity to a Cit-containing peptide. While the precise role of PAD4, and/or other PADs [e.g., PAD2], in the pathophysiology of RA is largely speculative, studies suggest that an elevated PAD activity is disease-causing in at least a subset of the patient population. The finding that PAD4 catalyzes the deimination of histones H2A, H3, and H4 has also drawn the attention of a broader community of scientists who are interested in characterizing the role of histone modifications in regulating gene transcription. In fact, it has recently been demonstrated that PAD4 acts as a transcriptional corepressor of the estrogen receptor and p53, and that the ability of PAD4 to alter gene transcription is peculiar to its catalytically active form.

Evidence linking dysregulated PAD activity to cancer includes the fact that PAD4 is overexpressed in variety of malignant tumors; however, this overexpression is not observed in the cells of benign tumors. Additionally, the levels of PAD4 are elevated in the blood of patients with malignant cancers, while the levels in patients with benign tumors remain normal. Interestingly, these levels decrease in patients with malignant tumors after these tumors have been resected. As in RA, the levels of citrullinated antithrombin are also elevated in patients with malignant cancers, a finding that is especially relevant given that thrombin activity increases the expression of both VEGF and integrin β3, thus contributing to angiogenesis, hyperplasia, and metastasis. PAD4 also acts as a transcriptional corepressor for p53, thus increased PAD4 activity could conceivably contribute to tumorgenesis both intra- and extracellularly.

In light of the evidence linking PAD activity to various disease states, it is conceivable, if not likely, that PAD-specific inhibitors could possess clinical utility for the treatment of RA, MS, and cancer. To date, a few inhibitors of PAD4 have been described in the literature. Of the known PAD inhibitors currently reported in the literature, two haloacetamidine-based compounds are the most potent described to date, F— and Cl— amidine (FIG. 2)—these two inactivators convalently modify the active site cysteine of the enzyme. Given the successful inhibition of PAD activity that was achieved with these inhibitors, elaboration of such structures in an effort to develop inhibitors with even greater potency would be beneficial.

In view of the above, a need exists for inhibitors with even greater potency for inhibition of PAD activity.

SUMMARY

In accordance with certain embodiments of the present disclosure, an inactivator of protein arginine deiminase is described. The inactivator includes:

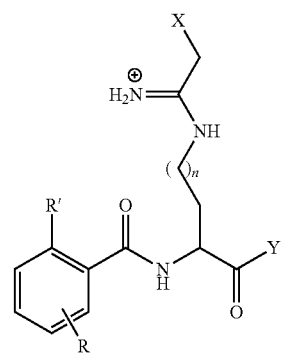

wherein x is F, Cl, or H;
wherein y is OH or NH$_2$;
wherein R$^1$ is a negatively charged moiety;
wherein R is H, an alkyl group, an alkenyl group, or an alknyl group;
and n is greater than 0.

In still other embodiments of the present disclosure, a method for inactivating protein arginine deiminase is described. The method includes contacting protein arginine deiminase with an inactivator.

Other features and aspects of the present disclosure are discussed in greater detail below.

BRIEF DESCRIPTION OF THE DRAWINGS

A full and enabling disclosure, including the best mode thereof, directed to one of ordinary skill in the art, is set forth more particularly in the remainder of the specification, which makes reference to the appended figures in which:

FIG. 3 illustrates the synthesis of ortho-carboxy-haloacetamidine inhibitors.

FIG. 8 illustrates potential inhibitor structures.

FIG. 9 presents the inhibitory effects of F-amidine, Cl-amidine, o-F-amidine, and o-Cl-amidine.

FIG. 10 presents cytotoxicity data for o-F-amidine and o-Cl-amidine in combination with Doxorubicin in HL-60 cells.

DETAILED DESCRIPTION

Figure 1:
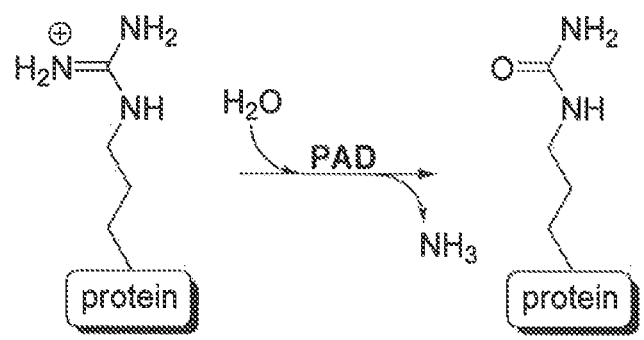
FIG. 1 illustrates PAD catalyzed hydrolysis of arginine residues to citrulline.
Figure 2:
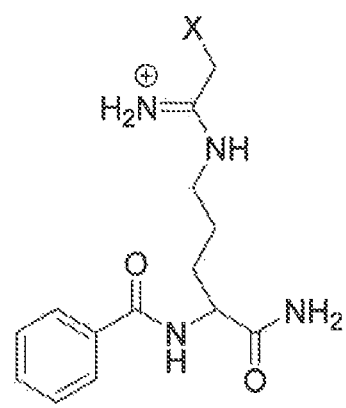
FIG. 2 illustrates the structure of X-amidines: F-amidine (X=F); Cl-amidine (X=Cl).

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

Examination of the PAD4 crystal structure shows an arginine residue near the opening of the enzyme active site. Because the side chain of this arginine residue is positively charged at physiological pH, in accordance with the present disclosure it has been postulated that the binding affinity of the X-amidine inhibitors could be increased by exploiting a charge-charge interaction with this residue.

Examination of the crystal structure of PAD4 with benzoyl-arginine-amide (BAA) reveals that the guanidinium portion of an arginine residue is in close proximity to the benzoyl portion of BAA. This observation prompted the design of an inhibitor that contains a negatively charged moiety on the benzoyl ring that will interact with this residue. In accordance with the present disclosure, it is believed that this charge-charge interaction increases the binding affinity of the inhibitor, and therefore increases the potency of the previously described haloacetamidine based inhibitors (i.e., F- and Cl-amidine). An example of the synthesis of such novel o-carboxy-haloacetamidine inhibitors is the orthogonally protected Fmoc-Orn(Boc)-OH (FIG. 3). Attachment of this amino acid to Rink AM amide resin using a standard solid phase peptide synthesis protocol enables convenient installation of the 2-carboxyl-benzoyl group and, upon cleavage from the resin, results in the formation of terminal amide moiety. Cleavage of the ornithine derivative from the resin with TFA also removes the Boc protecting group, thus revealing the side chain amine that is subsequently functionalized with the haloacetamidine-warhead. Installation of the warhead proceeds in solution in quantitative yield (FIG. 3).

The inhibitory effects of o-F- and o-Cl-amidine on PAD4 activity were tested using a previously described assay as further described in Luo, Y.; Knuckley, B.; Lee, Y. H.; Stallcup, M. R.; Thompson, P. R. J Am Chem Soc 2006, 128, 1092-1093, incorporated by reference herein. The $IC_{50}$ value of o-F-amidine against PAD4 is ~2 µM, which reflects a ~10-fold increase in potency over F-amidine. Interestingly, the $IC_{50}$ value for o-Cl-amidine was also ~2 µM against PAD4, representing a ~3-fold increase in potency over Cl-amidine. The $k_{inact}$, $K_1$, and $k_{inact}/K_1$ values for each of these inhibitors were subsequently determined (FIG. 9).

Figure 4:
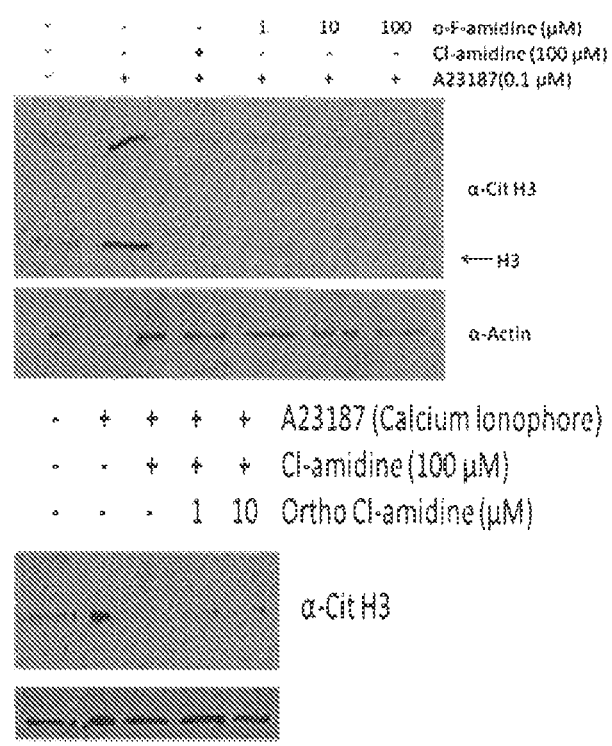
FIG. 4 illustrates that treatment of MCF-7 cells with haloacetamidine-based inhibitors results in reduced levels of deiminated histone H3.

Initial experiments were also conducted to determine the bioavailability of these two inhibitors. For these experiments, MCF-7 cells were treated with increasing amounts of inhibitors, after which time, the concentration of deiminated histone H3, a known substrate of PAD4, was analyzed. The results of these experiments show decreased levels of citrullinated H3, which is a clear indication of the in vivo inhibition of PAD4 (FIG. 4).

Figure 5:
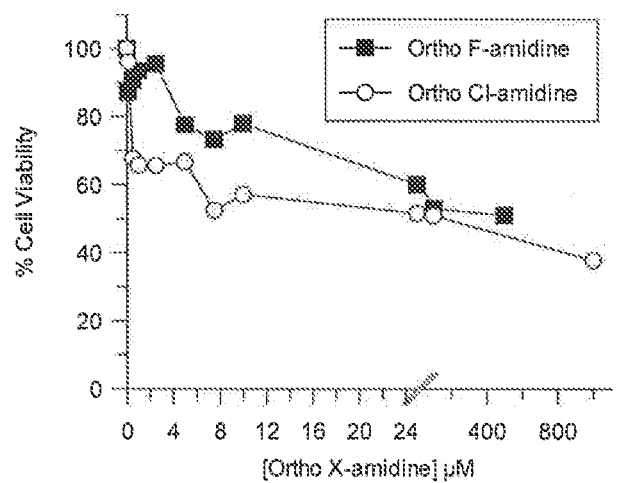
FIG. 5 illustrates that o-F- and o-Cl-amidine reduce cell viability in HL-60 cells.
Figure 6:
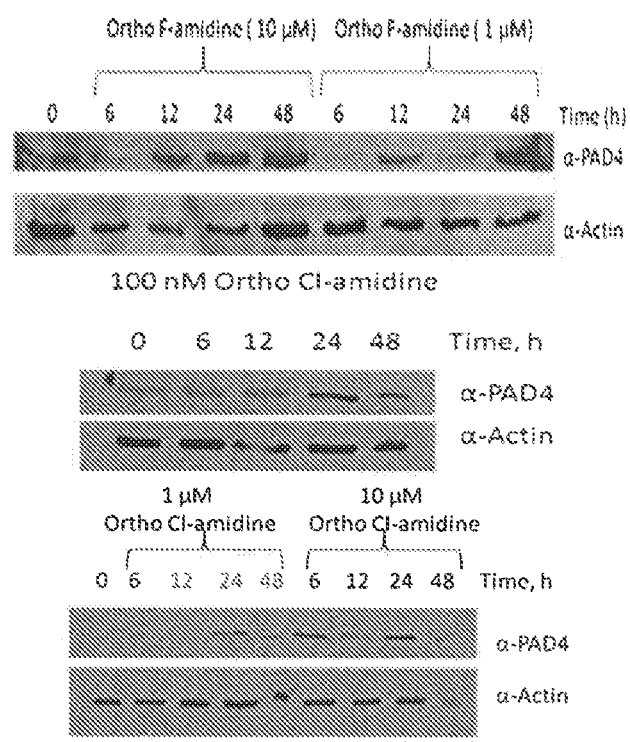
FIG. 6 illustrates that treatment with o-X-amidines causes increased expression of PAD4 in HL-60 cells indicating differentiation.

To further evaluate the in vivo effects of these compounds, their ability to inhibit the growth of HL60 cells, a leukemic cell line, was characterized. Interestingly, both compounds exhibit low-micromolar cytotoxic effects for these cells, however, complete cell killing was never achieved, even with increasing concentrations of inhibitor (FIG. 5). Such finding prompted further investigation into this phenomenon and led to the discovery that for the HL-60 cell line, the cells that remained viable were actually being differentiated into non-cancerous granulocytes. Evidence of this differentiation includes the increased expression of PAD4 (FIG. 6).

Figure 7A:
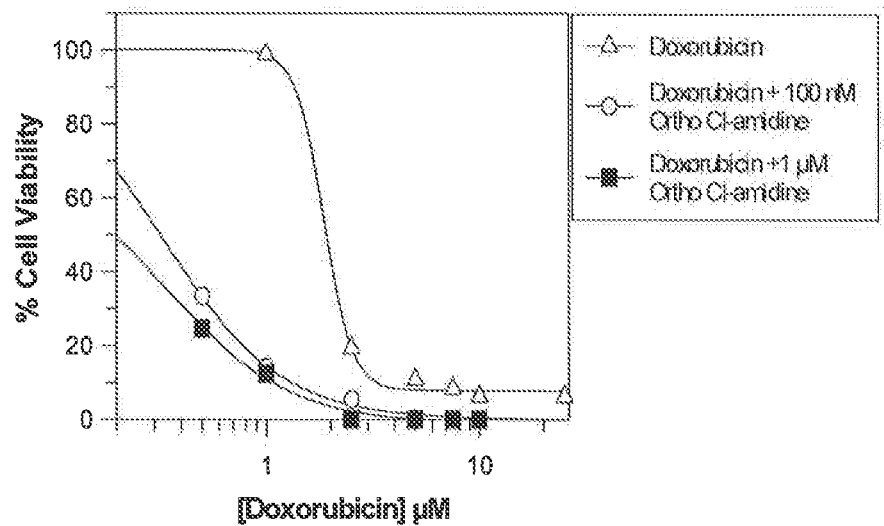
FIG. 7 illustrates that the effects of doxorubicin are potentiated by o-Cl-amidine (FIG. 7A) and by o-F-amidine (FIG. 7B) in HL-60 cells.
Figure 7B:
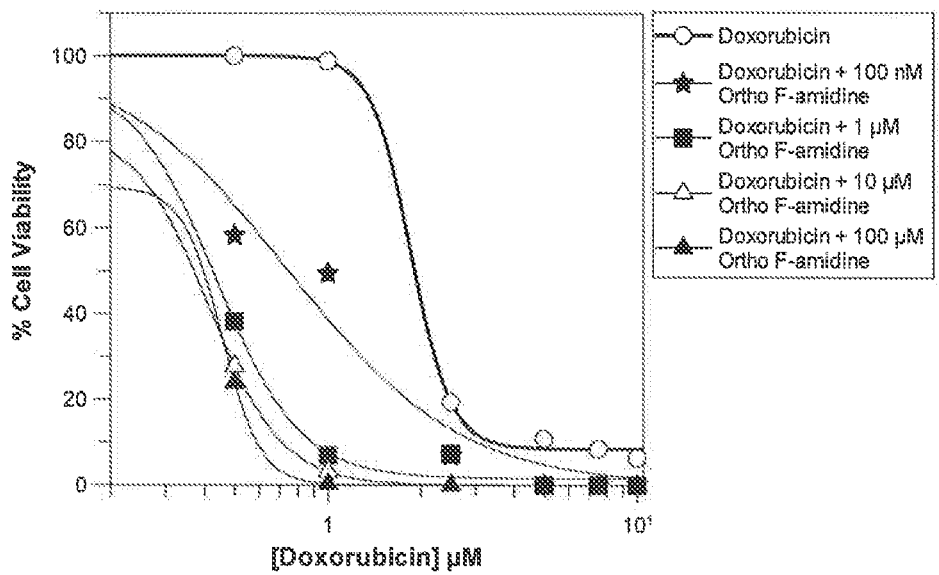

Although o-F- and o-Cl-amidine show some efficacy for killing cancer derived cells, the overall effects are modest. In light of such results, these inhibitors were tested in a combination with doxorubicin, a known chemotherapeutic that is used for the treatment of numerous cancers, often as part of a combination therapy. In accordance with the present disclosure, the additive effects of doxorubicin was tested with varying concentrations of both o-F- and o-Cl-amidine on HL-60 cell viability. The results of these experiments demonstrate that, when used in combination with the o-X-amidine inhibitors, the cell killing effects of doxorubicin are increased synergistically. This combination treatment induces complete cell killing on a short timescale, and at significantly lower doses of doxorubicin (FIG. 7A, FIG. 7B, FIG. 10).

Thus, the present disclosure describes the development of two novel PAD inhibitors/inactivators. These compounds are the most potent inhibitors of PAD4 activity known to date. In addition to demonstrating the inhibitory effects of these compounds in vitro, the present disclosure illustrates the in vivo applicability of such compounds. Each of these inhibitors exhibits modest cytotoxicity towards cells of cancerous lineage without affecting non-cancerous cells. The present disclosure also demonstrates that, in addition to killing a subset of cancerous cells, treatment of HL-60 cells with the described inhibitors also triggers cell differentiation into non-cancerous granulocytes. Combination treatment studies using o-F- and o-Cl-amidines, in conjunction with doxorubicin, show that the viability of cancer cells is reduced to levels that are undetectable above the background signal.

Taken together, the results of the experiments of the present disclosure indicate that o-F- and o-Cl-amidine show real potential as therapeutic agents for cancer, RA, and other diseases where dysregulated PAD activity plays a causative role, including MS. Furthermore, fluorescent conjugates of o-F- and o-Cl-amidine can be used as activity based protein profiling reagents; as such these compounds will facilitate investigations into the in vivo roles of PADs. Additionally, these compounds can be utilized for high-throughput fluorescence polarization assays to identify novel inhibitors from large libraries.

In accordance with the present disclosure, further elaboration of the compounds described herein may also lead to the discovery of more potent inhibitors of the PAD enzymes. These elaborations include additional substitutions about the benzyl ring, changes to the sidechain between the α-carbon and warhead moiety, and substitutions to the terminal amide (FIG. 8).

The present disclosure can be better understood with reference to the following examples.

EXAMPLES

Materials and Methods
N-α-(2-carboxyl)benzoyl-ornithine amide (TFA).

Rink Amide AM resin (300 mg, 0.186 mmol, 1 eq.) was suspended in 20% piperidine (in DMF) (5 mL) and gently rocked at r.t. for 20 min. The suspension was filtered and treated with 20% piperidine once more. After 20 min, the resin was filtered and washed with DMF (3×5 mL). Fmoc-Orn(Boc)-OH (338 mg, 0.74 mmol, 4 eq.), HBTU (282 mg, 0.74 mmol, 4 eq.) and HOBt (114 mg, 0.74 mmol, 4 eq.) were dissolved in DMF (5 mL) and N-methylmorpholine (0.164 mL, 1.49 mmol, 8 eq.) was added. After 10 min, this solution was added to the resin followed by gentle rocking. After 3 h, the resin was filtered, washed with DMF (3×5 mL) and treated with 20% piperidine (2×5 mL). The resin was then filtered, washed with DMF (3×5 mL) and resuspended in DMF (5 mL). After addition of phthalic anhydride (110 mg, 0.74 mmol, 4 eq.) and triethylamine (0.207 mL, 1.49 mmol, 8 eq.), the mixture was rocked at r.t. overnight. The resin was filtered, washed with DMF (3×5 mL), ethanol (3×5 mL) and dichloromethane (3×5 mL) and dried under vacuum. Cleavage and Boc-deprotection were accomplished by treatment with 10% TFA in DCM, followed by treatment with TFA/TIS/H$_2$O 95/2.5/2.5. The crude product was purified by RP-HPLC to afford the product as a white powder.
Ethylhaloacetimidate Hydrochloride.

Haloacetonitrile (fluoro or chloro) (3.4 mmol) and dry ethanol (0.2 mL, 3.4 mmol) were dissolved in dry ether (5 mL) and the mixture was cooled to 0° C. Dry hydrogen chloride gas was bubbled through the solution until a white precipitate began to form. The reaction was allowed to warm to r.t. and stir overnight. The white crystalline precipitate was isolated by centrifugation, washed with ether, dried under vacuum, and used without further purification.

N-α-(2-carboxyl)benzoyl-N$^5$-(2-fluoro-1-iminoethyl)-L-ornithine amide (o-Cl-amidine)

N-α-(2-carboxyl)benzoyl-ornithine amide (TFA) (15 mg, 0.038 mmol) and ethylfluoroacetimidate hydrochloride (10.7 mg, 0.076 mmol) were dissolved in dry methanol (1 mL). Cesium carbonate (18.5 mg, 0.057 mmol) was added, and the solution was stirred at r.t. overnight. The reaction was quenched with TFA, diluted with H$_2$O and purified by RP-HPLC to afford the product as a white powder.

N-α-(2-carboxyl)benzoyl-N$^5$-(2-chloro-1-iminoethyl)-L-ornithine amide (o-F-amidine)

N-α-(2-carboxyl)benzoyl-ornithine amide (TFA) (11 mg, 0.028 mmol) and ethylchloroacetimidate hydrochloride (8.8 mg, 0.056 mmol) were dissolved in dry methanol (1 mL). Cesium carbonate (13.7 mg, 0.042 mmol) was added, and the solution was stirred at r.t. overnight. The reaction was quenched with TFA, diluted with H$_2$O and purified by RP-HPLC to afford the product as a white powder.
IC$_{50}$ Assays IC$_{50}$ values of compounds o-F- and o-Cl-amidine were determined with variable concentrations of each inhibitor in a reaction buffer containing 100 mM HEPES (pH 7.6), 50 mM NaCl, 250 μM TCEP, and 10 mM CaCl$_2$. Preincubation of the aforementioned reaction mixtures at 37° C. for 10 min was started by adding PAD4 to a final concentration of 0.2 μM. BAEE was added to a final concentration of 10 mM to initiate the reactions which were quenched after 15 min by flash freezing in liquid nitrogen. For color development, 200 μL of freshly prepared COLDER solution (2.25 M H$_3$PO$_4$, 4.5 M H$_2$SO$_4$, 1.5 mM NH$_4$Fe(SO$_4$), 20 mM diacetyl monoxime, and 1.5 mM thiosemicarbazide) was added to the quenched reactions, vortexed to ensure complete mixing, and then incubated at 95° C. for 30 min. The absorbance at 540 nm was then measured and compared to a Cit standard curve to determine the concentration of Cit produced during the course of the reactions. Assays were performed in duplicate and agreement within 20% was required for inclusion in this study. IC$_{50}$ values were determined by fitting the concentration-response data to Equation 1, $$\text{Fractional activity of } PAD4 = 1/(1+([I]/IC_{50})) \quad \text{(eq 1)}$$

The concentration of inhibitor that corresponds to the midpoint (fractional activity=0.5) was referred to as the IC$_{50}$.
Cell Lines and Cell Culture.

HL-60 human promyelocytic leukemia cells were obtained from the ATCC (Manassas, Va.). The cells were cultured in RPMI 1640 media supplemented with 10% FBS and 1% Pencillin-Streptomycin, in a 5% CO$_2$ incubator at 37° C. MCF-7 cells were cultured in DMEM media supplemented with 10% FBS and 1% Penicillin-Streptomycin, in a 5% CO$_2$ incubator at 37° C.
Bioavailability of o-F- and o-Cl-amidine MCF-7 cells (~5×10$^5$) were added to each well of a 12-well plate. Cells were allowed to adhere to the plate for 15 h at 37° C., 5% CO$_2$. The media was removed and replaced with Locke's solution (1 mL). Cl-amidine (100 μM), o-F-amidine (1-100 μM), o-Cl-amidine (1-100 μM), or PBS (control) were added to the cells. Cells were incubated with the inhibitors for 15 minutes at 37 C, 5% CO$_2$. After 15 minutes, the calcium ionophore, A23187 (4 μM) was added to the appropriate samples, and they were incubated for an additional 30 minutes at 37° C., 5% CO$_2$. Cells were rinsed with PBS and resuspended in an SDS lysis buffer (2% SDS, 62.5 mM Tris pH 6.8, 10% glycerol). Proteins were separated by 15% SDS-PAGE and transferred to a nitrocellulose membrane for western blot analysis. Membranes were blocked with 5% Nonfat dry milk in TBST for 1 h at room temperature. The membranes were probed with polyclonal anti-Citrulline H3 antibody (Abcam, ab5103) or a polyclonal anti-actin antibody (Abcam, ab1801).
Cytotoxicity.

HL-60 and MCF-7 cells were grown to confluence (1×10$^6$ cells/mL) in the appropriate media. 50 μL of the MCF-7 cells were plated into each well of a 96 well plate with 40 μL of DMEM. Cells were allowed to adhere to the plate for 15 h at 37° C. and 5% CO$_2$. For the HL-60 cells, 90 μL of the cells were added to each well of a 96 well plate. o-F-amidine, o-Cl-amidine, doxorubicin, or ATRA (10 μL, 100 nM to 100 μM) were added to the plates and allowed to incubate with the cells for 24 h. Cell viability was determined using the CellTiter 96 Non-radioactive Cell Proliferation Assay (Promega). Cell viability was quantified as the percentage of control absorbance. Each condition was performed in triplicate. The use of 1% triton served as a 100% killing control. When possible, $EC_{50}$ values were determined by fitting the dose response data to equation 2 using GraFit (version 5.0.11)[33], $$\text{Fractional Activity}=1/(1+([I]/EC_{50})) \quad \text{(eq 2)}$$

where [I] is the concentration of inhibitor (e.g., doxorubicin) and $EC_{50}$ is the concentration of inhibitor that yields half-maximal cell survival.

Western Blotting.

HL-60 cells (~5×10[5]) were added to each well of a 12-well plate and treated for 0-48 h with either: ATRA (1 μM), o-Cl-amidine (100 nM, 1 μM, 100 μM), o-F-amidine (100 nm, 1 μM, 100 μM), or PBS as a negative control. Cells were collected after 6, 12, 24, and 48 h by centrifugation at 1000 rpm for 5 min at 4° C. Cells were rinsed twice with cold PBS and resuspended in SDS lysis buffer (2% SDS, 62.5 mM Tris pH 6.8 and 10% glycerol) and boiled to afford cell lysis and protein denaturation. Proteins were then separated by 12% SDS-PAGE and transferred to PVDF for western blot analysis. The membranes were blocked with either 5% Nonfat dry milk or 5% BSA for 1 h at room temperature. The membranes were probed with either a polyclonal anti-PAD4 antibody (Abcam ab38772), or a polyclonal anti-actin antibody (Abcam, ab1801).

In the interests of brevity and conciseness, any ranges of values set forth in this specification are to be construed as written description support for claims reciting any sub-ranges having endpoints which are whole number values within the specified range in question. By way of a hypothetical illustrative example, a disclosure in this specification of a range of 1-5 shall be considered to support claims to any of the following sub-ranges: 1-4; 1-3; 1-2; 2-5; 2-4; 2-3; 3-5; 3-4; and 4-5.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only, and is not intended to limit the disclosure.

What is claimed is:
1. An inactivator of protein arginine deiminase, the inactivator comprising:

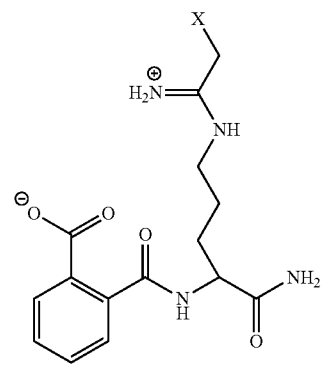

wherein x comprises F, or Cl.
2. The inactivator of claim 1, wherein x comprises F.
3. The inactivator of claim 1, wherein x comprises Cl.
4. A method for inactivating protein arginine deiminase 4, the method comprising:
contacting protein arginine deiminase 4 with an inactivator, the inactivator comprising

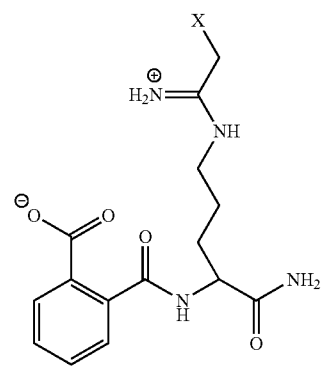

wherein x comprises F or Cl.
5. The method of claim 4, wherein x comprises F.
6. The method of claim 4, wherein x comprises Cl.
7. The method of claim 4, further comprising administering a chemotherapeutic agent with the inactivator.
8. The method of claim 4, wherein the chemotherapeutic agent comprises doxorubicin.
9. The method as in claim 4, wherein the method is performed in vivo.

* * * * *